(12) United States Patent
Sun et al.

(10) Patent No.: US 10,709,810 B2
(45) Date of Patent: *Jul. 14, 2020

(54) PROCESSED ADIPOSE TISSUE (71) Applicant: LifeCell Corporation, Branchburg, NJ (US)

(72) Inventors: Wenquan Sun, Warrington, PA (US); Xianghong Liu, Hillsborough, NJ (US)

(73) Assignee: LifeCell Corporation, Madison, NJ (US)

(*) Notice: Subject to any disclaimer, the term of this patent is extended or adjusted under 35 U.S.C. 154(b) by 76 days.

This patent is subject to a terminal disclaimer.

(21) Appl. No.: 15/159,220

(22) Filed: May 19, 2016

(65) Prior Publication Data
US 2016/0256606 A1 Sep. 8, 2016

Related U.S. Application Data (63) Continuation of application No. 14/036,369, filed on Sep. 25, 2013, now Pat. No. 9,370,536.

(60) Provisional application No. 61/705,789, filed on Sep. 26, 2012.

(51) Int. Cl.
A61L 27/36 (2006.01)
A61K 35/35 (2015.01)
A61F 2/12 (2006.01)

(52) U.S. Cl.
CPC ............ *A61L 27/3604* (2013.01); *A61F 2/12* (2013.01); *A61K 35/35* (2013.01); *A61L 27/3695* (2013.01); *A61L 2430/40* (2013.01)

(58) Field of Classification Search
CPC ............ A61L 27/3604; A61L 27/3695; A61L 2430/40; A61F 2/12; A61K 35/35
See application file for complete search history.

(56) References Cited

U.S. PATENT DOCUMENTS

| | | | |
|---|---|---|---|
| 4,233,969 A | 11/1980 | Lock et al. | |
| 4,373,519 A | 2/1983 | Errede et al. | |
| 4,569,348 A | 2/1986 | Hasslinger | |
| 4,582,640 A | 4/1986 | Smestad et al. | |
| 4,681,571 A | 7/1987 | Nehring | |
| 4,703,108 A | 10/1987 | Silver et al. | |
| 4,902,508 A | 2/1990 | Badylak et al. | |

(Continued)

FOREIGN PATENT DOCUMENTS

| | | |
|---|---|---|
| WO | WO-1990/00060 A1 | 1/1990 |
| WO | WO-2000/016822 A1 | 3/2000 |

(Continued)

OTHER PUBLICATIONS

Shlivko et al. Identification of layers in optical coherence tomography of skin: comparative analysis of experimental and Monte Carlo simulated images. Skin Res Technol, 2015 (21): 419-425.*

(Continued)

*Primary Examiner* — William H Matthews
(74) *Attorney, Agent, or Firm* — McCarter & English, LLP (57) ABSTRACT

The present disclosure provides tissue products produced from adipose-containing tissues, as well as methods for producing such tissue products. The tissue products can include decellularized and partially de-fatted tissues. In addition, the present disclosure provides systems and methods for using such products.

16 Claims, 3 Drawing Sheets

(56) References Cited

U.S. PATENT DOCUMENTS

| | | | |
|---|---|---|---|
| 4,950,483 A | 8/1990 | Ksander et al. |
| 4,969,912 A | 11/1990 | Kelman et al. |
| 5,104,957 A | 4/1992 | Kelman et al. |
| 5,131,850 A | 7/1992 | Brockbank |
| 5,149,331 A | 9/1992 | Ferdman et al. |
| 5,160,313 A | 11/1992 | Carpenter et al. |
| 5,231,169 A | 7/1993 | Constantz et al. |
| 5,254,133 A | 10/1993 | Seid |
| 5,263,971 A | 11/1993 | Hirshowitz et al. |
| 5,275,826 A | 1/1994 | Badylak et al. |
| 5,284,655 A | 2/1994 | Bogdansky et al. |
| 5,298,015 A | 3/1994 | Komatsuzaki et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,437,651 A | 8/1995 | Todd et al. |
| 5,489,304 A | 2/1996 | Orgill et al. |
| 5,549,584 A | 8/1996 | Gross |
| 5,613,982 A | 3/1997 | Goldstein |
| 5,632,778 A | 5/1997 | Goldstein |
| 5,636,643 A | 6/1997 | Argenta et al. |
| 5,641,518 A | 6/1997 | Badylak et al. |
| 5,645,081 A | 7/1997 | Argenta et al. |
| 5,681,561 A | 10/1997 | Hirshowitz et al. |
| 5,728,752 A | 3/1998 | Scopelianos et al. |
| 5,739,176 A | 4/1998 | Dunn et al. |
| 5,800,537 A | 9/1998 | Bell |
| 5,893,888 A | 4/1999 | Bell |
| 5,901,717 A | 5/1999 | Dunn et al. |
| 5,993,844 A | 11/1999 | Abraham et al. |
| 6,027,743 A | 2/2000 | Khouri et al. |
| 6,071,267 A | 6/2000 | Zamierowski |
| 6,071,747 A | 6/2000 | Strosberg et al. |
| 6,096,347 A | 8/2000 | Geddes et al. |
| 6,113,623 A | 9/2000 | Sgro |
| 6,135,116 A | 10/2000 | Vogel et al. |
| 6,179,872 B1 | 1/2001 | Bell et al. |
| 6,194,136 B1 | 2/2001 | Livesey et al. |
| 6,326,018 B1 | 12/2001 | Gertzman et al. |
| 6,345,623 B1 | 2/2002 | Heaton et al. |
| 6,371,992 B1 | 4/2002 | Tanagho et al. |
| 6,432,710 B1 | 8/2002 | Boss, Jr. et al. |
| 6,485,723 B1 | 11/2002 | Badylak et al. |
| 6,553,998 B2 | 4/2003 | Heaton et al. |
| 6,576,265 B1 | 6/2003 | Spievack |
| 6,666,892 B2 | 12/2003 | Hiles et al. |
| 6,814,079 B2 | 11/2004 | Heaton et al. |
| 6,840,960 B2 | 1/2005 | Bubb |
| 6,933,326 B1 | 8/2005 | Griffey et al. |
| 7,070,584 B2 | 7/2006 | Johnson et al. |
| 7,198,046 B1 | 4/2007 | Argenta et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,700,819 B2 | 4/2010 | Ambrosio et al. |
| 7,763,769 B2 | 7/2010 | Johnson et al. |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,100,874 B1 | 1/2012 | Jordan et al. |
| 8,110,216 B2 | 2/2012 | Ambrosio et al. |
| 8,152,783 B2 | 4/2012 | Swain |
| 8,163,974 B2 | 4/2012 | Ambrosio et al. |
| 8,197,551 B2 | 6/2012 | Swain et al. |
| 8,197,806 B2 | 6/2012 | Girouard et al. |
| 8,257,372 B2 | 9/2012 | Swain et al. |
| 8,267,918 B2 | 9/2012 | Johnson et al. |
| 8,324,449 B2 | 12/2012 | McQuillan et al. |
| 2002/0103542 A1 | 8/2002 | Bilbo |
| 2002/0120185 A1 | 8/2002 | Johnson |
| 2003/0035843 A1 | 2/2003 | Livesey et al. |
| 2003/0143207 A1 | 7/2003 | Livesey et al. |
| 2003/0162707 A1 | 8/2003 | Fraser et al. |
| 2003/0225347 A1 | 12/2003 | Argenta et al. |
| 2004/0037735 A1 | 2/2004 | DePaula et al. |
| 2005/0028228 A1 | 2/2005 | McQuillan et al. |
| 2005/0043819 A1 | 2/2005 | Schmidt et al. |
| 2005/0159822 A1 | 7/2005 | Griffey et al. |
| 2006/0073592 A1 | 4/2006 | Sun et al. |
| 2006/0127375 A1 | 6/2006 | Livesey et al. |
| 2006/0153816 A1 | 7/2006 | Brown et al. |
| 2006/0210960 A1 | 9/2006 | Livesey et al. |
| 2007/0078522 A2 | 4/2007 | Griffey et al. |
| 2007/0104759 A1 | 5/2007 | Dunn et al. |
| 2007/0219471 A1 | 9/2007 | Johnson et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2008/0114277 A1 | 5/2008 | Ambrosio et al. |
| 2009/0035289 A1 | 2/2009 | Wagner et al. |
| 2009/0157017 A1 | 6/2009 | Ambrosio |
| 2009/0198167 A1 | 8/2009 | Ambrosio |
| 2009/0220579 A1 | 9/2009 | Hassingboe et al. |
| 2009/0287181 A1 | 11/2009 | Kagan |
| 2009/0306790 A1 | 12/2009 | Sun |
| 2009/0326515 A1 | 12/2009 | Kagan |
| 2010/0021961 A1 | 1/2010 | Fujisato et al. |
| 2010/0040687 A1 | 2/2010 | Pedrozo et al. |
| 2010/0168689 A1 | 7/2010 | Swain et al. |
| 2010/0168720 A1 | 7/2010 | Swain et al. |
| 2010/0168870 A1 | 7/2010 | Swain et al. |
| 2010/0179515 A1 | 7/2010 | Swain et al. |
| 2010/0209408 A1 | 8/2010 | Stephen et al. |
| 2010/0272782 A1 | 10/2010 | Owens et al. |
| 2011/0020271 A1 | 1/2011 | Niklason et al. |
| 2011/0152196 A1* | 6/2011 | Shah ............... A61L 27/3633 514/17.2 |
| 2011/0184357 A1 | 7/2011 | Robinson et al. |
| 2011/0198353 A1 | 8/2011 | Tsao |
| 2011/0251566 A1 | 10/2011 | Zimnitsky et al. |
| 2012/0010728 A1 | 1/2012 | Sun et al. |
| 2012/0040013 A1 | 2/2012 | Owens et al. |
| 2012/0189588 A1 | 7/2012 | Nahas et al. |
| 2012/0263763 A1 | 10/2012 | Sun et al. |
| 2013/0053960 A1 | 2/2013 | Park et al. |
| 2013/0121970 A1 | 5/2013 | Owens et al. |
| 2013/0158676 A1 | 6/2013 | Hayzlett et al. |
| 2014/0341871 A1* | 11/2014 | Morris ............... A61L 27/362 424/93.21 |
| 2016/0331504 A1* | 11/2016 | Wang ............... A61F 2/0063 |

FOREIGN PATENT DOCUMENTS

| | | | |
|---|---|---|---|
| WO | WO-2000/047114 A1 | 8/2000 | |
| WO | WO-2002/40630 A2 | 5/2002 | |
| WO | WO-2003/017826 A2 | 3/2003 | |
| WO | WO-2003/032735 A1 | 4/2003 | |
| WO | WO-2005/009134 A1 | 2/2005 | |
| WO | WO-2007/043513 A1 | 4/2007 | |
| WO | WO-2007/134134 A2 | 11/2007 | |
| WO | WO-2009/009620 A2 | 1/2009 | |
| WO | WO-2010/019753 A2 | 2/2010 | |
| WO | WO-2010/078353 A2 | 7/2010 | |
| WO | WO-2011/019822 A2 | 2/2011 | |
| WO | WO 2011019822 A2 * | 2/2011 | ............ A61K 31/00 |
| WO | WO-2012/019103 A2 | 2/2012 | |
| WO | WO-2012/083412 A1 | 6/2012 | |
| WO | WO-2012/142419 A1 | 10/2012 | |
| WO | WO-2012/166784 A1 | 12/2012 | |

OTHER PUBLICATIONS

Ahn et al., "The past, present, and future of xenotransplantation" *Yonsei Med J.*, 45(6):1017-1024 (Dec. 31, 2004).

Allman et al., "Xenogeneic Extracellular Matrix Grafts Elicit a TH2-Restricted Immune Response" *Transplantation*, 71 (11):1631-1640 (Jun. 15, 2001).

Argenta, L.C. et al. "Vacuum-Assisted Closure: A New Method for Wound Control and Treatment: Clinical Experience" *Annals of Plastic Surgery*, 38(6):563-577 (Jun. 1997).

(56) References Cited

OTHER PUBLICATIONS

Aycock et al., "Parastomal Hernia Repair With Acellular Dermal Matrix" *J. Wound Ostomy Continence Nurs.*, 34(5):521-523 (2007).
Badylak et al., "Endothelial cell adherence to small intestinal submucosa: An acellular bioscaffold" *Biomaterials*, 20:2257-2263 (1999).
Badylak et al., "Extracellular Matrix As a Biological Scaffold Material: Structure and Function" *Acta Biomaterialia*, 5(1):1-13 (2009).
Beniker et al., "The use of acellular dermal matrix as a scaffold for periosteum replacement" *Orthopedics*, 26(5 Suppl):s591-s596 (May 2003).
Blackburn II, J.H. et al. "Negative-Pressure Dressings as a Bolster for Skin Grafts" Annals of Plastic Surgery, 40(5):453-457 (May 1998).
Brandi, C. et al. "Treatment with vacuum-assisted closure and cryo-preserved homologous de-epidermalised dermis of complex traumas to the lower limbs with loss of substance, and bones and tendons exposure" *Journal of Plastic, Reconstructive and Aesthetic Surgery*, 61(12):1507-1511 (2008).
Bruder et al., "The Effect of Implants Loaded with Autologous Mesenchymal Stem Cells on the Healing of Canine Segmental Bone Defects" *J. Bone Joint Surg.*, 80:985-986 (1998).
Buma et al., "Tissue engineering of the meniscus" *Biomaterials*, 25(9):1523-1532 (2004).
Chaplin et al., "Use of an Acellular Dermal Allograft for Dural Replacement: An Experimental Study" *Neurosurgery*, 45(2):320-327 (Aug. 1999).
Chariker, M.E. et al. "Effective management of incisional and cutaneous fistulae with closed suction wound drainage" Contemporary Surgery, 34:59-63 (Jun. 1989).
Chen et al. "Acellular Collagen Matrix As a Possible 'Off the Shelf' Biomaterial for Urethral Repair" *Urology*, 54(3):407-410 (1999).
Chinn, S.D. et al. "Closed Wound Suction Drainage" *The Journal of Foot Surgery*, 24(1):76-81 (1985).
Collins et al., "Cardiac xenografts between primate species provide evidence for the importance of the α-galactosyl determinant in hyperacute rejection" *J. Immunol.*, 154:5500-5510(1995).
Costantino et al., "Human Dural Replacement With Acellular Dermis: Clinical Results and a Review of the Literature" *Head & Neck*, 22:765-771 (Dec. 2000).
Dagalakis, N. et al. "Design of an artificial skin. Part III. Control of pore structure" *J. Biomed. Mater. Res.*, 14:511-528 (1980).
Crapo et al., "An overview of tissue and whole organ decellularization process," Biomaterials, 32(12):3233-3243 (Apr. 2011).
Dattilo Jr., P.P. et al. "Medical Textiles: Application of an Absorbable Barbed Bi-directional Surgical Suture" *Journal of Textile and Apparel, Technology and Management*, 2(2):1-5 (Spring 2002).
Defranzo, AJ. et al. "Vacuum-Assisted Closure for the Treatment of Abdominal Wounds" *Clinics in Plastic Surgery*, 33(2):213-224 (Apr. 2006).
Dobrin et al., "Elastase, collagenase, and the biaxial elastic properties of dog carotid artery" *Am. J. Physiol. Heart Circ. Physiol.*, 247:H124-H131 (1984).
Edel, "The use of a connective tissue graft for closure over an immediate implant covered with occlusive membrane" *Clin. Oral Implants Res.*, 6:60-65 (1995) (Abstract).
European Search Report and Search Opinion issued in Application No. 1115636.8, dated Jul. 5, 2011.
Flack, S. et al. "An economic evaluation of VAC therapy compared with wound dressings in the treatment of diabetic foot ulcers" *J. Wound Care*, 17(2):71-78 (Feb. 2008).
Fowler et al., "Ridge Preservation Utilizing an Acellular Dermal Allograft and Demineralized Freeze-Dried Bone Allograft: Part II. Immediate Endosseous Impact Placement" *J. Periodontol.*, 71: 1360-1364 (2000).
Fowler et al., "Root Coverage with an Acellular Dermal Allograft: A Three-Month Case Report" *J. Contemp. Dental Pract.*, 1 (3):1-8 (2000).

Galili et al., "Interaction Between Human Natural Anti-a-Galactosyl Immunoglobulin G and Bacteria of the Human Flora" *Infect. Immun.*, 56(7):1730-1737 (1988).
Galili et al., "Interaction of the Natural Anti-Gal Antibody with α-Galactosyl Epitopes: a Major Obstacle for Xenotransplantation in Humans" Immunology Today, 14(10) :480-482 (1993).
Galili et al., "Man, Apes, and Old World Monkeys Differ from Other Mammals in the Expression of α-Galactosyl Epitopes on Nucleated Cells" *J. Biol. Chem.*, 263(33):17755-17762 (1988).
Gamba et al. "Experimental abdominal wall defect repaired with acellular matrix" *Pediatr. Surg. Int.*, 18:327-331 (2002).
Gebhart et al., "A radiographical and biomechanical study of demineralized bone matrix implanted into a bone defect of rat femurs with and without bone marrow" *Acta Orthop. Belg.*, 57(2):130-143 (1991) (Abstract).
Griffey, S. et al. "Particulate Dermal Matrix as an Injectable Soft Tissue Replacement Material" *J. Biomed. Mater. Res. (Appl. Biomater.)*, 58:10-15 (2001).
Hammond et al., "Parastomal Hernia Prevention Using a Novel Collagen Implant: A Randomised Controlled Phase 1 Study" *Hernia*, 12:475-481 (2008).
International Search Report and Written Opinion for PCT/US2013/041111, dated Aug. 29, 2013.
International Search Report and Written Opinion for PCT/US2013/061563, dated Nov. 19, 2013.
International Search Report and Written Opinion issued in International Patent Application No. PCT/US2009/053667, dated Oct. 12, 2010.
International Search Report and Written Opinion issued in International Patent Application No. PCT/US2012/039969, dated Jul. 30, 2012.
Invitation to Pay Additional Fees with Partial International Search Report issued in International Patent Application No. PCT/US2009/053667, dated Jun. 17, 2010.
Ju, Y.M. et al., "Beneficial Effect of Hydrophilized Porous Polymer Scaffolds in Tissue-Engineered Cartilage Formation" *J. Biomed. Mater. Res. Part B: Appl. Biomater.*, 85B:252-260 (2008; online Oct. 31, 2007).
KCI Licensing, Inc. "VAC.® Therapy Safety Information" 2007, pp. 1-4.
Kish et al., "Acellular Dermal Matrix (AlioDerm): New Material in the Repair of Stoma Site Hernias" *The American Surgeon*, 71:1047-1050 (Dec. 2005).
Kridel et al., "Septal Perforation Repair with Acellular Human Dermal Allograft" *Arch. Otolaryngol. Head Neck Surg.*, 124:73-78 (Jan. 1998).
Laidlaw et al., "Tympanic Membrane Repair With a Dermal Allograft" *Laryngoscope*, 111:702-707 (Apr. 2001).
Lee et al., "In vitro evaluation of a poly(lactide-co-glycolide)-collagen composite scaffold for bone regeneration" *Biomaterials*, 27:3466-3472 (2006).
Lu et al., "Novel Porous Aortic Elastin and Collagen Scaffolds for Tissue Engineering" *Biomaterials*, 25(22):5227-5237 (2004).
Masters, J. "Reliable, Inexpensive and Simple Suction Dressings" Letters to the Editor, *British Journal of Plastic Surgery*, 51 (3):267 (1998).
O'Brien, F.J. et al., "The effect of pore size on cell adhesion in collagen-GAG scaffolds" *Biomaterials*, 26:433-441 (2005).
O'Connor, J. et al. "Vacuum-Assisted Closure for the Treatment of Complex Chest Wounds" Ann. Thorac. Surg., 79:1196-1200 (2005).
Randall, K.L. et al. "Use of an Acellular Regenerative Tissue Matrix in Combination with Vacuum-assisted Closure Therapy for Treatment of a Diabetic Foot Wound" Journal of Foot and Ankle Surgery, 47(5):430-433 (2008).
Simon et al., "Early failure of the tissue engineered porcine heart valve SYNERGRAFT™ in pediatric patients" *Eur. J. Cardiothorac. Surg.*, 23(6):1002-1006 (2003).
Smith et al., Plastic and Reconstructive Surgery, May 2006, vol. 117, No. 6, pp. 1836-1844.
U.S. Appl. No. 12/540,489 by Pedrozo et al.: 2012.
U.S. Appl. No. 12/540,489 by Pedrozo et al.: Dec. 21, 2011.

(56) References Cited

OTHER PUBLICATIONS

Wei, H-J. et al. "Construction of varying porous structures in acellular bovine pericardia as a tissue-engineering extracellular matrix" *Biomaterials*, 26(14):1905-1913 (2005; online Jul. 17, 2004).

Wu, Z. et al. "Preparation of collagen-based materials for wound dressing" *Chinese Medical Journal*, 116(3):419-423 (2003).

Xu, H. et al. "A Porcine-Derived Acellular Dermal Scaffold that Supports Soft Tissue Regeneration: Removal of Terminal Galactose-$\alpha$-(1,3)-Galactose and Retention of Matrix Structure" Tissue Engineering, 15:1-13 (2009).

Yang, Q. et al. "A cartilage ECM-derived 3-D porous acellular matrix scaffold for in vivo cartilage tissue engineering with PKH26-labeled chondrogenic bone marrow-derived mesenchymal stem cells" *Biomaterials*, 29(15):2378-2387 (Mar. 4, 2008).

Zheng et al. "Porcine small intestine submucosa (SIS) is not an acellular collagenous matrix and contains porcine DNA: Possible implications in human implantation" *J. Biomed. Mater. Res. B: Appl. Biomater.*, 73(1):61-67 (2005).

\* cited by examiner

PROCESSED ADIPOSE TISSUE

This application claims the benefit under 35 U.S.C. §§ 119 and 120 of U.S. Provisional Patent Application No. 61/705,789, filed on Sep. 26, 2012, and is a continuation of U.S. patent application Ser. No. 14/036,369, now U.S. Pat. No. 9,370,536, which was filed on Sep. 25, 2013, all of which are incorporated herein by reference.

The present disclosure relates to tissue products, and more particularly, to products containing extracellular tissue matrices made from adipose tissue.

Various tissue-derived products are used to regenerate, repair, or otherwise treat diseased or damaged tissues and organs. Such products can include tissue grafts and/or processed tissues (e.g., acellular tissue matrices from skin, intestine, or other tissues, with or without cell seeding). Such products generally have properties determined by the tissue source (i.e., the tissue type and animal from which it originated) and the processing parameters used to produce the tissue products. Since tissue products are often used for surgical applications and/or as tissue replacements or for augmentation, the products should support tissue growth and regeneration and avoid excess inflammation, as desired for the selected implantation site. The present disclosure provides adipose tissue products that can provide for improved tissue growth, revascularization, and regeneration in various applications, while improving surgical handling and reducing inflammation.

According to certain embodiments, methods for producing tissue products are provided. The methods include selecting an adipose-containing tissue; treating the tissue to remove substantially all cellular material from the tissue, and further processing the tissue to reduce the adipose content of the tissue. In addition, tissue products made by the disclosed processes are provided. The products can comprise a decellularized adipose extracellular tissue matrix and a reduced lipid content. The tissue product can be provided in a sheet format that is suitable for surgical use and/or for further manipulation to prepare a desired implant shape, or can be provided in any other desired shape.

Furthermore, methods of treatment are provided. The methods can comprise placing an adipose tissue product into a surgical site to replace, repair, regenerate, augment, and/or enhance a native tissue. The tissue product can be formed into a predetermined three-dimensional shape and implanted into the host tissue at the desired location.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products have been produced for regeneration, repair, reinforcement, and/or treatment of human tissues that have been damaged or lost due to various diseases and/or structural damage (e.g., from trauma, surgery, atrophy, and/or long-term wear and degeneration). Likewise, such products have been used to augment or enhance various tissues. Such products can include, for example, acellular tissue matrices, tissue allografts or xenografts, and/or reconstituted tissues (i.e., at least partially decellularized tissues that have been seeded with cells to produce viable materials). For example, ALLODERM® and STRATTICE™ (LifeCell Corp., Branchburg, N.J.) are two dermal acellular tissue matrices made from human and porcine dermis, respectively.

Although such materials are very useful for treating certain types of conditions, materials having different biological and mechanical properties may be desirable for certain applications. For example, ALLODERM® and STRATTICE™ may not be ideal for regeneration, repair, replacement, and/or augmentation of certain soft tissues or adipose-containing tissues following the removal of bulk tissue volume (e.g., a volume of at least about 1, 2, 5, 10, 20, 50, 100, 200, 1000 ml or more of tissue). Accordingly, the present disclosure provides tissue products that can be placed into a surgical site to replace, repair, regenerate, augment, and/or enhance a native adipose-containing tissue or other soft tissue. The present disclosure also provides methods for producing such tissue products.

The tissue products of the present disclosure can include adipose-containing tissues that have been processed to removal at least some of the cellular components. In some cases, all (or substantially all) cellular material is removed, while retaining some or substantially all of the extracellular matrix components (e.g., collagen, elastin, or other fibers, as well as proteoglycans, polysaccharides and growth factors). In addition, the tissue products can be further processed to remove some of the extracellular and/or intracellular lipids. As described in further detail below, the tissue product can be provided in sheet form or any other desired three dimensional shapes. In addition, to allow for treatment of a selected tissue site, the material can be further processed (e.g., by E-beam or gamma irradiation) to reduce bioburden on the tissue product.

As noted, the tissue products of the present disclosure are derived from adipose-containing tissues. The adipose-containing tissues can be from human or animal sources, and from any tissue that contains adipose (e.g., a tissue containing a substantial number of adipocytes, such as a tissue in which the lipid content accounts for at least about 20% of the overall tissue mass). For example, human adipose-containing tissue can be obtained from one or more cadavers, e.g., from dermal or subdermal sources. Suitable human tissue can also be obtained from live donors (e.g., with an autologous tissue). In addition, while the adipose-containing tissue may be derived from one or more donor animals of the same species as the intended recipient animal, this is not necessarily the case. Thus, for example, the tissue product may be prepared from an animal tissue and implanted in a human patient. Species that can serve as donors and/or recipients of acellular tissue include, without limitation, humans, nonhuman primates (e.g., monkeys, baboons, or chimpanzees), pigs, cows, horses, goats, sheep, dogs, cats, rabbits, guinea pigs, gerbils, hamsters, rats, or mice. In some embodiments, tissue from more than one donor animal can be used.

If animal sources are used, the tissues may be further treated (e.g., using enzymatic processes) to remove antigenic components such as 1,3-alpha-galactose moieties, which are present in, e.g., pigs, but not in humans or primates and may result in an immune response following implantation. In addition, the adipose-containing tissue can be obtained from animals that have been genetically modified to remove antigenic moieties. See Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009). For further descriptions of appropriate animals and methods of producing transgenic animals for xenotransplantation, see U.S. patent application Ser. No. 10/896,594 and U.S. Pat. No. 6,166,288, which are hereby incorporated by reference in their entirety.

In certain embodiments, the adipose-containing tissue is provided from transitional dermal tissue layers between the dermis and the subcutaneous fat. In some embodiments, the adipose-containing tissue comprises approximately 20-90% lipid content by mass prior to the processing described below. In certain embodiments, the adipose-containing tissue comprises 20, 25, 30, 35, 40, 45, 50, 55, 60, 65, 70, 75, 80, 85, or 90% lipid content by mass prior to processing (or any percentage in between). In certain embodiments, the adipose-containing tissue also comprises 1-10% extracellular matrix (ECM) components (e.g., collagen, elastin, or other fibers, as well as proteoglycans, polysaccharides and growth factors) by mass prior to processing. In certain embodiments, the adipose-containing tissue comprises 1, 2, 3, 4, 5, 6, 7, 8, 9, or 10% ECM components by mass prior to processing (or any percentage in between). In certain embodiments, the chosen adipose-containing tissue is a dermal tissue (e.g., tissue from transitional tissue layers between the dermis and subcutaneous fat) because these tissues provide a sufficiently high ECM content as well as a high lipid content suitable for further processing.

Once an adipose-containing tissue has been provided, the tissue can be processed to form a tissue product. In various embodiments, the processing includes partial or complete decellularization and partial lipid removal (i.e., a partial reduction in the lipid content). In some embodiments, both processes are performed simultaneously. In other embodiments, the adipose-containing tissue is first decellularized and then lipids are partially removed, or vice versa.

In various embodiments, the adipose-containing tissue is washed to remove any residual cryoprotectants, red blood cells, and/or any other contaminants. Solutions used for washing can be any physiologically-compatible solution. Examples of suitable wash solutions include distilled water, phosphate buffered saline (PBS), or any other biocompatible saline solution. In some embodiments, the tissue is then decellularized by the addition of one or more detergents to the wash solution in order to remove cells and cellular material. Exemplary methods for decellularizing tissue are disclosed in U.S. Pat. No. 6,933,326 and U.S. Patent Application 2010/0272782, which are hereby incorporated by reference in their entirety.

In various embodiments, the general steps involved in the production of an acellular or partially decellularized adipose-containing tissue include providing adipose-containing tissue from a donor (e.g., a human or animal source) and removing cellular material under conditions that preserve some or all of the biological and/or structural components of the extracellular matrix.

In certain embodiments, the adipose-containing tissue can be chemically treated to stabilize the tissue so as to avoid biochemical and/or structural degradation before, during, or after cell removal. In various embodiments, the stabilizing solution arrests and prevents osmotic, hypoxic, autolytic, and/or proteolytic degradation; protects against microbial contamination; and/or reduces mechanical damage that may occur during decellularization of the tissue. The stabilizing solution can contain an appropriate buffer, one or more antioxidants, one or more antibiotics, one or more protease inhibitors, and/or one or more smooth muscle relaxants.

In various embodiments, the adipose-containing tissue is placed in a decellularization solution to remove viable and non-viable cells (e.g., epithelial cells, endothelial cells, smooth muscle cells, fibroblasts, etc.) and cellular components without damaging the biological and/or structural integrity of the extracellular matrix. For example, enzymes, detergents, and/or other agents may be used in one or more steps to remove cellular materials and/or other antigenic materials. The decellularization solution may contain an appropriate buffer, salt, an antibiotic, one or more detergents (e.g., TRITON X-100™, Tris[2-(dimethylamino)ethyl] amine, sodium dodecyl sulfate, sodium deoxycholate, polyoxyethylene (20) sorbitan mono-oleate, etc.), one or more agents to prevent cross-linking, one or more protease inhibitors, and/or one or more enzymes. In some embodiments, the decellularization solution comprises about 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of TRITON X-100™ and, optionally, about 10 mM, 15 mM, 20 mM, 25 mM, 30 mM, 35 mM, 40 mM, 45 mM, or 50 mM EDTA (ethylenediaminetetraacetic acid) (or any concentration in between). In certain embodiments, the decellularization solution comprises about 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of sodium deoxycholate and, optionally, about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, or 20 mM HEPES buffer (4-(2-hydroxyethyl)-1-piperazineethanesulfonic acid) containing about 10 mM, 15 mM, 20 mM, 25 mM, 30 mM, 35 mM, 40 mM, 45 mM, or 50 mM EDTA (or any concentrations in between). In some embodiments, the tissue is incubated in the decellularization solution at about 20, 21, 22, 23, 24, 25, 30, 31, 32, 33, 34, 35, 36, 37, 38, 39, 40, 41, 42, 43, 44, 45, 46, 47, 48, 49, or 50 degrees Celsius (or at any temperature in between), and optionally, gentle shaking is applied at about 10, 20, 30, 40, 50, 60, 70, 80, 90, 100, 110, 120, 130, 140, or 150 rpm (or any rpm in between). The incubation can be for about 1, 2, 3, 4, 5, 6, 7, 8, 9, 10, 11, 12, 15, 20, 24, 36, 48, or 96 hours (or any time in between).

In various embodiments, the length of time of exposure to the decellularization solution and/or the concentration of detergent or other decellularizing agents can be adjusted in order to partially or more fully decellularize the tissue. In some embodiments, substantially all of the cellular material is removed (e.g., at least about 80, 85, 90, 95, 98, 99, 99.5, or 99.9% of the cellular material is removed). In certain embodiments, additional detergents and combinations of detergents may be used to remove cells from the adipose-containing tissue. For example, in certain embodiments, a combination of sodium deoxycholate and TRITON X-100™ are used. In various embodiments, the decellularization process does not alter the structure and/or function of the extracellular matrix in the adipose-containing tissue. For example, the structure of the extracellular matrix in the decellularized tissue can remain substantially unaltered when compared to non-decellularized tissue. In some embodiments, further proteolytic processing is employed to remove undesirable extracellular matrix components. For example, alpha-galactosidase can be applied to remove alpha-galactose moieties.

In certain embodiments, e.g., when xenogenic or allogenic material is used, the decellularized tissue can optionally be treated overnight at room temperature with a deoxyribonuclease (DNase) solution. In some embodiments, the tissue sample is treated with a DNase solution prepared in a DNase buffer (e.g., about 20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable DNase buffer can be used, as long as the buffer provides for suitable DNase activity.

In certain embodiments, after decellularization, viable cells may optionally be seeded in the extracellular matrix of the partially or completely decellularized adipose-containing tissue. In some embodiments, viable cells may be added by standard in vitro cell co-culturing techniques prior to transplantation, or by in vivo repopulation following transplantation. In vivo repopulation can be by the migration of native cells from surrounding tissue into the ECM of a tissue product following implantation, or by infusing or injecting viable cells obtained from the recipient or from another donor into the tissue product in situ. Various cell types can be used, including stem cells such as embryonic stem cells and/or adult stem cells. Any other viable cells can also be used. In some embodiments, the cells are mammalian cells. In certain embodiments, the cells are histocompatible with the subject in which they are implanted. Such cells can promote native cell and/or tissue migration, proliferation, and/or revascularization. In various embodiments, the cells can be directly applied to the ECM of a tissue product just before or after implantation.

In various embodiments, the adipose-containing tissue in a tissue product can be processed to partially remove lipid components. For example, the adipose-containing tissue can be partially de-fatted by exposing the tissue to an elevated temperature, to ultrasonic energy, or to a combination of the two in order to melt or otherwise remove a desired percentage of lipids. For example, the tissue can be exposed to temperatures of about 40-50° C. (e.g., about 40, 41, 42, 43, 44, 45, 46, 47, 48, 49, or 50° C.) for up to about 24 hours (e.g., about 1, 2, 3, 4, 5, 10, 15, 20, or 24 hours, or any time period in between) in order to remove a desired percentage or type of fat, especially unsaturated fat species. In some embodiments, the temperature used or the length of exposure can be increased in order to increase the amount of lipids removed, or can be decreased in order to reduce the amount of lipids removed. The adipose-containing tissue can also be exposed to ultrasonic energy in order to remove lipids. For example, the tissue can be exposed to ultrasonic energy of about 20 to 2000 watts per square meter (e.g., about 20, 40, 60, 80, 100, 200, 500, 1000, or 2000 watts per square meter, or any value in between). The ultrasonic energy can be at a frequency of about 20 to 400 kilohertz (e.g., about 20, 40, 60, 80, 100, 150, 200, 250, 300, 350, or 400 kHz), and the exposure duration can be about 30 seconds to 8 hours (e.g., 30 seconds, 45 seconds, or 1, 5, 10, 30, or 60 minutes, or 1, 2, 3, 4, 5, 6, 7, or 8 hours, or any time period in between). The tissue can be exposed to ultrasonic energy alone or in combination with high temperatures, in order to remove a desired percentage of lipids. In some embodiments, the energy level used or the length of exposure can be increased in order to increase the amount of lipids removed, or can be decreased in order to reduce the amount of lipid removed. In some embodiments, a combination of high temperature and ultrasonic energy can be used. In certain embodiments, one or more detergents, such as sodium dodecyl sulfate or Tris[2-(dimethylamino)ethyl] amine, can be used in combination with high temperature and/or ultrasonic energy to assist in lipid removal.

In various embodiments, the decellularization and lipid removal processes can occur simultaneously. Alternatively, decellularization can be carried out first or lipid removal can be done first.

In some embodiments, after decellularization and partial lipid removal, the adipose-containing tissue is washed thoroughly. Any physiologically compatible solutions can be used for washing. Examples of suitable wash solutions include distilled water, phosphate buffered saline (PBS), or any other biocompatible saline solution. In some embodiments, the wash solution can contain a disinfectant. In certain embodiments, the disinfectant is peracetic acid (PAA), for example, at a concentration of about 0.05, 0.1, 0.15, 0.2, 0.25, 0.3, 0.4, or 0.5% (or any percentage in between).

In some embodiments, following the decellularization and partial lipid removal processes, the tissue product can contain about 20-70% lipid content (as a percentage of the overall tissue product by mass), and preferably contains about 30-50% lipid content by mass. In some embodiments, the tissue product contains about 20, 30, 40, 50, 60, or 70% lipid content by mass following processing (or any percentage in between).

In various embodiments, the tissue product is processed to remove sufficient lipids such that the product can avoid significant inflammatory and/or immunologic responses following implantation (e.g., by removing lipids such that the tissue product comprises less than about 60% lipid content). Significant inflammation encompasses any inflammation that would hinder the long-term ability of the implant to promote native cell repopulation and host tissue repair, regeneration, treatment, or healing. Inflammation can be evaluated, for example, by measuring the level of one or more inflammatory marker in a sample taken from a patient (e.g., the level of one or more inflammatory cells, cytokines, immunoglobulins, or other inflammatory molecules in a blood or tissue sample) and comparing that level to one or more reference levels.

In certain embodiments, the tissue product retains sufficient lipid content such that the product can provide a soft and malleable material suitable for filling the potentially irregular shape of an implant site (e.g., by retaining at least about 20% lipid content in the tissue product).

In some embodiments, following decellularization and partial lipid removal, the tissue product contains an increased amount of ECM as a percentage of the overall tissue product by mass. In certain embodiments the tissue product contains about 3-20% ECM by mass. In some embodiments, the tissue product contains about 3, 4, 5, 6, 7, 8, 9, 10, 15, or 20% ECM by mass (or any percentage in between). In certain embodiments, the tissue product comprises sufficient ECM following decellularization and partial lipid removal such that the ECM can provide structural support and integrity for the lipid components of the tissue product (e.g., sufficient structural support such that the tissue product comprises a solid material rather than a shapeless and greasy mass of adipose). For example, the ECM can provide structural support such that the tissue product can be provided in sheets, thereby allowing for improved surgical handling and manipulation before and/or during implantation. In some embodiments, the ECM in an adipose tissue product also provides a scaffold into which native cells and vasculature can migrate and proliferate from tissue surrounding an implant after surgical implantation into a host.

After decellularization and partial lipid removal, a tissue product can be further processed to provide a desired three dimensional shape (e.g., a sheet of tissue product). In some embodiments, a tissue product can be further processed to provide an anatomical shape useful for implanting into a host tissue. For example, a spherical or cylindrical shape can be provided where the tissue product will be implanted following removal of a similarly shaped volume of native tissue.

In some embodiments, the adipose tissue product can be treated to reduce bioburden (i.e., to reduce the number of microorganisms growing on the tissue). In some embodiments, the treated tissue product lacks substantially all bioburden (i.e., the tissue product is aseptic or sterile). Suitable bioburden reduction methods are known to one of skill in the art, and may include exposing the tissue product to radiation. Irradiation may reduce or substantially eliminate bioburden. In some embodiments, an absorbed dose of about 14-18 kGy of e-beam radiation or 25-30 kGy of gamma irradiation is delivered in order to reduce or substantially eliminate bioburden. In various embodiments, a tissue product is exposed to between about 5 Gy and 50 kGy of radiation (e.g., about 5, 10, 15, 20, 25, 30, 35, 40, 45, or 50 kGy, or any value in between). Suitable forms of radiation can include gamma radiation, E-beam radiation, and X-ray radiation. In some embodiments, E-beam irradiation is used. Other irradiation methods are described in U.S. Application 2010/0272782, the disclosure of which is hereby incorporated by reference in its entirety.

In certain embodiments, one or more additional agents can be added to the adipose tissue product. In some embodiments, the additional agent can comprise an anti-inflammatory agent, an analgesic, or any other desired therapeutic agent. In certain embodiments, the additional agent can comprise at least one added growth or signaling factor (e.g., a cell growth factor, an angiogenic factor, a differentiation factor, a cytokine, a hormone, and/or a chemokine). In some embodiments, these additional agents can promote native tissue migration, proliferation, and/or vascularization within the ECM of a tissue product following implantation. In some embodiments, the growth or signaling factor is encoded by a nucleic acid sequence contained within an expression vector. Preferably, the expression vector is in one or more of the viable cells that can be added, optionally, to the tissue product. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, termination codon, etc.) to ensure at least minimal expression of the desired protein by the cell.

In various embodiments, the tissue products described above have the ability to support the migration and proliferation of native cells into the extracellular matrix in the tissue product following implantation, as well as the ability to promote the regeneration, revascularization, repair, and/or treatment of native tissue when implanted in or on a patient. In addition, the tissue products have the ability to act as a carrier for and support the growth of cells, including stems cell, such as adipose-derived stem cells. Accordingly, in certain embodiments, the processes discussed above should not alter the extracellular matrix proteins of the adipose-containing tissue (e.g., by damaging protein structures and/or removing important glycosaminoglycans and/or growth factors). In some embodiments, the products will have normal collagen banding as evidenced by transmission electron microscopy.

In some embodiments, an adipose tissue product can be stored in a suitable aqueous solution or can be freeze-dried for long-term storage. The specific freeze drying protocol can vary depending on the solvent used, sample size, and/or to optimize processing time. One suitable freeze-drying process can include freezing the tissue product to −35° C. over a 45 minute period; holding the samples at −35° C. for 90 minutes to insure complete freezing; applying a vacuum; raising the temperature to −10° C. and holding for 24 hours; raising the temperature to 0° C. and holding for 24 hours; and raising the temperature to 20° C. and holding for 12 hours. The freeze-dried samples can then be removed from the freeze-dryer and packaged in foil pouches under nitrogen.

Use of Tissue Products

The adipose tissue products described herein can be used to treat a variety of different anatomic sites. For example, the tissue products can be implanted to fill a void space in a native tissue (e.g., following injury or surgical removal of a bulk volume of native tissue, such as after surgical removal of a tumor). Similarly, the tissue products can be used as implants or in conjunction with polymeric implants for use in cosmetic procedures to augment or enhance a native tissue. For example, the tissue products of the present disclosure are produced from adipose-containing tissues. Accordingly, it is believed that the adipose tissue products will provide superior regenerative capabilities when implanted in certain tissue sites, as compared to materials produced from other tissue types. For example, the retained lipid components in the partially de-fatted tissue products are believed to promote the deposition and storage of lipids within and around the implanted product, while the ECM components of the implanted product provide a scaffold for the migration and proliferation of native cells within the implant, thereby allowing for the regeneration of more natural looking and/or feeling tissue around the implant site. The implanted tissue products can also promote revascularization. Accordingly, in certain embodiments, the tissue products disclosed herein can be implanted in tissue sites in a host human or other animal that predominantly or significantly comprise adipose tissue, and the implanted products can promote the repair, regeneration, treatment, augmentation, and/or enhancement of the host tissue.

In some embodiments, the tissue sites for implantation of an adipose tissue product can include a breast (e.g., for augmentation, enhancement, replacement of resected tissue, or placement around an implant). In addition, a site in any other adipose or soft tissue can be selected. For example, the tissue products may be used for reconstructive or cosmetic purposes in the face, neck, buttocks, abdomen, hips, thighs, and/or any other site comprising adipose or soft tissue where reconstruction or augmentation is desired using a tissue product having a structure and/or feel that approximates that of native adipose. In any of those sites, the tissue may be used to reduce or eliminate wrinkles, sagging, or undesired shapes.

When used as implants to repair, regenerate, treat, augment, and/or enhance adipose or other soft tissues, the tissue products disclosed herein can provide advantages over other implanted natural and synthetic products. For example, although some tissue implants allow for native cell ingrowth and tissue formation (e.g., implants from non-adipose tissue sources that comprise an extracellular matrix), those implants may induce the formation of fibrotic tissue that does not mimic normal texture and/or feel of adipose or other soft tissues, and may appear abnormal on radiologic imaging. Since the tissue products of the present disclosure are formed from adipose-containing tissues, they may avoid or reduce the extent of fibrotic tissue formation. Furthermore, since the tissue products retain some lipid components following partial lipid removal, it is believed that the implanted products promote the deposition of native adipose and are less likely to harden over time, thereby retaining the look and/or feel of native adipose tissue. In contrast, adipose tissue implants that lack substantially all lipid components (e.g., less than 20% of the adipose present prior to processing) may result in stiff implant materials that lack sufficient malleability for use as soft tissue fillers, and which may also harden further over time.

In addition, as discussed above, the tissue products disclosed herein can be provided in sheets or other desired three-dimensional shapes that retain structural integrity and provide for ease of surgical manipulation. The tissue products disclosed herein do not, in certain embodiments, require micronization, homogenization, or further processing (e.g., freeze drying and/or cross-linking) in order to provide for malleable yet structurally stable tissue implants that do not induce significant immune and/or inflammatory responses, in contrast to certain full-fat implants. Such full-fat implants may have a viscous consistency and cannot retain a desired shape, and may also have an increased possibility of inducing an immune and/or inflammatory response. In contrast, the partially de-fatted tissue products disclosed herein promote native lipid deposition while avoiding the inflammatory and immunologic responses that may be associated with implanted adipose tissues that have not been de-fatted.

EXAMPLES

The following examples serve to illustrate, and in no way limit, the present disclosure.

Example 1: Determining Lipid Content

To determine lipid content, tissue samples were washed with 0.9% NaCl, and then with mini-Q water. Washed tissue was freeze-dried. Lipid from the freeze-dried samples was extracted with chloroform. Extracted tissue samples were vacuum-dried. The loss of sample mass due to extraction was used to determine lipid content. The lipid content was calculated using the formula:

$$\text{Lipid Content (\%)} = (\text{Initial Dry Weight} - \text{Extracted Dry Weight})/(\text{Initial Dry Weight}) \times 100$$

Example 2: Decellularization and Partial Lipid Removal of Porcine Dermis

Layers of porcine adipose tissue at a depth of between 2.75 mm and 4.20 mm was obtained for processing. The lipid content of the adipose tissue samples was determined to be 85.9±6.8% (mean±SD, N=8) on a dry mass basis. The loose fat on the tissue surface was scraped manually, and the tissue was pre-incubated for 22 hours with gentle agitation in 35% maltodextrin solution containing 0.24 g/L cefoxitin, 0.12 g/L licomycin, 0.03 g/L vancomycin and 0.1 g/L polymyxin B sulfate. The scrapping and incubation reduced the tissue lipid content to 74.8±12.6% (mean±SD, N=7) on a dry mass basis. The tissue was stored at −80° C. until used.

For further processing, frozen tissue material was thawed at 4° C. over a period of 65 hours. After washing twice with 20 mM HEPES buffer (pH 8.0) to remove the maltodextrin solution, the tissue was decellularized for ~20 hours in 1% (w/v) sodium deoxycholate dissolved in 10 mM HEPES buffer (pH 8.1) containing 0.3% (w/v) Triton X100, with agitation. Decellularized tissue was rinsed with 10 mM HEPES buffer (pH 7.2) containing 10 mM $MgCl_2$ and 10 mM $CaCl_2$. DNAse and alpha galactosidase were then added at 4 mg/L and 2 mg/L, respectively for treatment for 20 hours. The resultant tissue matrix was washed three times in HEPES buffer (pH 7.2) over 8 hours to remove residual enzymes. The processing steps resulted in a further reduction of lipid content. Processed tissue was stored in 4 mM citrate-phosphate buffer (pH 6.5) containing 12% (w/v) glycerol, and terminally sterilized by 26 kGy gamma irradiation.

The average thickness of sterilized adipose tissue matrix sheets was 1.0±0.2 mm, which is thinner than the starting material due to partial lipid removal during processing. The soft adipose matrix had a moderate tensile strength of 2.7±1.6 MPa (mean±SD, N=48). Residual DNA content was 0.073±0.041 µg/g (mean±SD, N=10) on a dry mass basis, indicating the removal of greater than 99.5% of the DNA in the tissue. Immunostaining with lectin was negative for the presence of alpha-gal antigen. Lipid content, non-fat tissue matrix density, and water content of the sterilized adipose tissue matrices were measured to be 37.0±6.2%, 11.8±2.5%, and 51.3±3.8% (mean±SD, n=5), respectively.

Example 3: Ultrasound-Facilitated Decellularization

Ultrasound was used to aid in the process of decellularization and partial lipid removal. The first method involved treatment of tissue before decellularization in sodium deoxycholate solution. The tissue was exposed to high ultrasonic energy for 30 seconds (~95 Watts per square inch). Ultrasound-treated tissue was then decellularized in 1% (w/v) sodium deoxycholate solution.

The second method involved decellularization of tissue material in a lower energy ultrasonic water bath (Bransonic ultrasonic cleaner, 44 kilohertz, ~1.0 Watt per square inch) for up to 8 hours. Porcine dermal tissue was decellularized in two different solutions: (a) 1% sodium deoxycholate +0.5% Triton X-100 in 10 mM HEPES buffer (pH 8.0) and (b) 1% sodium dodecyl sulfate 10 mM HEPES buffer (pH 8.0).

Example 4: Control of Temperature During Ultrasonic Decellularization

Figure 1:
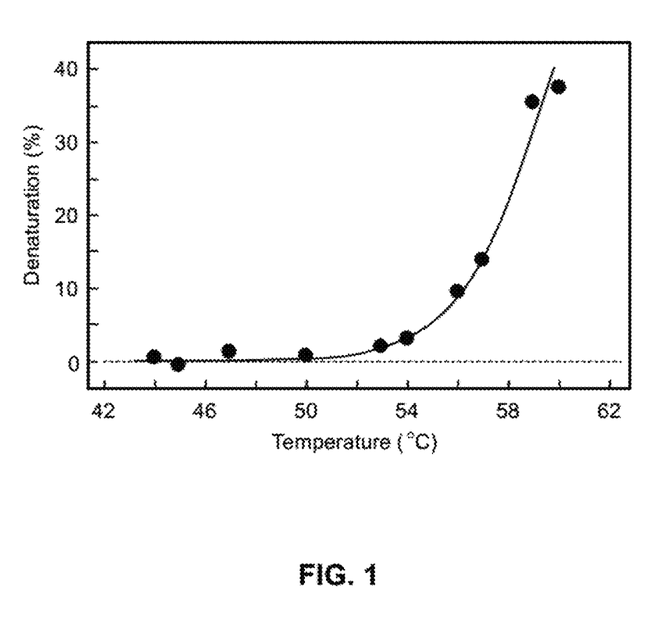
FIG. 1 is a plot showing differential scanning calorimetry data indicating the percentage of collagen denaturation in tissue samples, prepared according to certain embodiments of the present disclosure, after incubation at different temperatures. Tissue samples were scanned from 2° C. to 120° C. at 4° C./min.

Ultrasonic treatment generates heat and could lead to an increase in temperature of decellularization solution. To avoid denaturation of adipose tissue material, the solution temperature was controlled to keep it below a threshold above which collagen denaturation may occur. To determine the appropriate temperature, tissue samples were incubated for 60 minutes at different temperatures between 44° C. and 60° C. After incubation, the extent of collagen denaturation was measured with differential scanning calorimeter. During the calorimetric test, tissue samples were scanned from 2° C. to 120° C. at 4° C./min. FIG. 1. No denaturation was observed for tissues incubated at temperatures below 50° C. Thus, the tissue processing temperature can be raised above 40° C. to accelerate the decellularization process.

Example 5: In Vivo Performance

Figure 2:
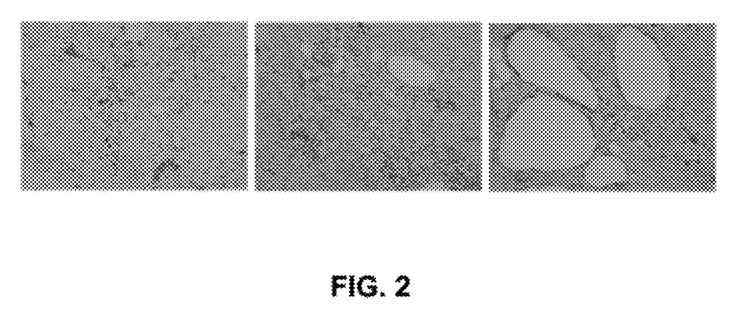
FIG. 2 shows Hematoxylin and eosin (H&E) staining of sections taken from adipose tissue products with different lipid content (63%, 45% and 72%, from left to right) three months after implantation in African green monkeys, according to certain embodiments of the present disclosure. Sections were prepared using tissues from the center of grafts, and the images are at 200× magnification.
Figure 3:
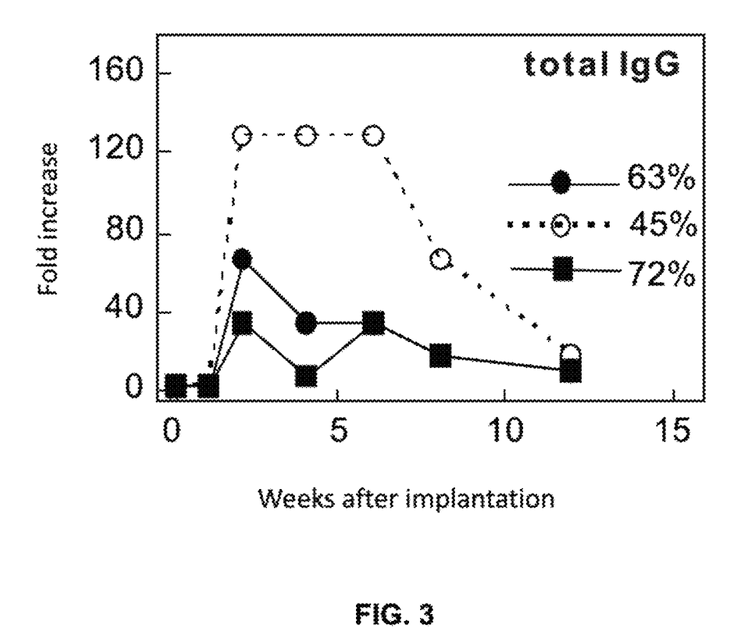
FIG. 3 shows systemic antibody (IgG) titer in African green monkey serum over time following implantation of one of three adipose tissue products with different lipid content (63%, 45% and 72% on a dry mass basis, respectively), according to certain embodiments of the present disclosure.

The in vivo performance of processed adipose tissue grafts with high lipid content of between about 45% and 75% on a dry mass basis was evaluated using a primate functional abdominal wall repair model (African green monkey). Three such grafts with different lipid content (45%, 63%, and 72%) were implanted for three months, and blood samples were taken at 0, 1, 2, 4, 6, 8, and 12 weeks after implantation. There was no herniation in any of the animals, and all three grafts integrated well with surrounding animal tissues. Histological analysis of explanted materials demonstrated host cell repopulation and re-vascularization. FIG. 2 shows the H&E stained sections of the three grafts after explantation at 3 months. No inflammation was observed in the graft with 45% lipid content (on a dry weight basis). Significant inflammation was observed only in the graft with about 70% lipid content (on a dry weight basis). The tests of blood samples taken after implantation showed that the quantity of IgG antibodies was low with a transient increase (<128 folds) following surgery, indicating that grafts induced insignificant immunological reactions (FIG. 3).

The in vivo primate evaluation demonstrated that tissue grafts with high lipid content were able to integrate into host tissues and to support cell repopulation and re-vascularization. As lipid content increased (>about 70%), however, inflammation became more severe. The primates did not have significant foreign body reactions to the grafts.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A method of producing a tissue product, comprising:
   providing a sheet of tissue comprising adipose-containing transitional dermis;
   treating the sheet of tissue to remove substantially all cellular material from the tissue; and
   processing the sheet of tissue to partially remove lipid components such that the tissue product retains at least about 35% lipid content as a percentage of the overall tissue product by mass following processing.

2. The method of claim 1, wherein the sheet of tissue comprises about 40-90% lipid content as a percentage of the overall tissue product by mass prior to processing.

3. The method of claim 1, wherein substantially all cellular material is removed using one or more detergents.

4. The method of claim 3, wherein the one or more detergents comprise at least a polyethylene glycol, Tris[2-(dimethylamino)ethyl]amine, sodium dodecyl sulfate, sodium deoxycholate, and polyoxyethylene (20) sorbitan mono-oleate.

5. The method of claim 1, wherein processing the sheet of tissue to partially remove lipid components comprises exposing the sheet of tissue to an elevated temperature of about 40-50° C., to ultrasonic energy, or a combination of the elevated temperature and the ultrasonic energy.

6. The method of claim 1, wherein the tissue product comprises at least about 3% extracellular matrix components as a percentage of the overall tissue product by mass following processing.

7. The method of claim 1, further comprising exposing the tissue product to E-beam radiation.

8. The method of claim 1, wherein processing the sheet of tissue to partially remove lipid components includes processing the sheet of tissue such that the tissue product contains between 35% and 50% lipid content as a percentage of the overall tissue product by mass.

9. A tissue product, comprising:
   a sheet of decellularized adipose-containing transitional dermal matrix,
   wherein a portion of lipid components have been removed from the sheet of decellularized adipose-containing transitional dermal matrix such that the tissue product retains at least about 35% lipid content as a percentage of the overall tissue product by mass.

10. The tissue product of claim 9, wherein the tissue product has at most about 70% lipid content as a percentage of the overall tissue product by mass.

11. The tissue product of claim 9, wherein the tissue product has at least about 3% extracellular matrix components as a percentage of the overall tissue product by mass.

12. A method of treatment comprising:
   selecting a tissue site in a patient; and
   implanting the tissue product of claim 9 on or into the tissue site.

13. The method of claim 12, wherein the tissue site comprises adipose tissue or soft tissue.

14. The method of claim 12, wherein the tissue site comprises a breast.

15. The method of claim 14, wherein the tissue product is implanted to augment a tissue site.

16. The method of claim 12, wherein the tissue site is a breast, a face, a buttock, an abdomen, a hip, or a thigh.

* * * * *